United States Patent [19]

Weijand

[11] Patent Number: 5,772,605
[45] Date of Patent: Jun. 30, 1998

[54] SYSTEM AND METHOD FOR DETECTING FACIAL SYMMETRY

[75] Inventor: Koen Weijand, Hoensbroek, Netherlands

[73] Assignee: Medtronic, Inc., Minneapolis, Minn.

[21] Appl. No.: 768,686

[22] Filed: Dec. 18, 1996

[51] Int. Cl.⁶ .................................................. A61B 5/00
[52] U.S. Cl. ........................................................ 600/547
[58] Field of Search ................................. 600/546, 547, 600/383, 382; 607/139, 140

[56] References Cited

U.S. PATENT DOCUMENTS

| | | | |
|---|---|---|---|
| 3,789,834 | 2/1974 | Duroux | 128/2.1 Z |
| 3,946,745 | 3/1976 | Hsiang-Lai et al. | 128/421 |
| 4,165,750 | 8/1979 | Aleev et al. | 128/422 |
| 4,589,417 | 5/1986 | Eseifan et al. | 128/422 |
| 4,595,010 | 6/1986 | Radke | 128/421 |
| 5,086,779 | 2/1992 | DeLuca et al. | 128/733 |
| 5,163,440 | 11/1992 | DeLuca | 128/733 |
| 5,427,113 | 6/1995 | Hiroshi | 128/734 |

OTHER PUBLICATIONS

Control of Paralysed Axial Muscles by Electrical Stimulation. Zealear DL; Dedo H. (Acta Otolaryngol Stockh) (Sweden) May–Jun. 1977, 83 (5–6) pp. 514–527 ISSN 0001–6489 Journal Code: 1HA.

Magnetic Stimulation of the Facial Nerve Yamakawa T; Yoshikawa H; Sakurai A; Ichikawa G Dept. of Otorhinolaryngology, Juntendo University, School of Medicine, Tokyo Nippon Jibilnkoka Gakkai kaiho (Japan) Sep. 1978, 86 (9) pp. 410–416 ISSN 0030–6622 Journal Code: JJZ.

Magnetic Stimulation of Facial Nerve Kartush JM; Bouchard KR; Graham MD; Linstrom CL; AM J Otology vol. 10, No. 1 Jan. 1989.

An Artificial Myotatic Reflex: A Potential Avenue to Fine Motor Control Gundfest; Broniatowski; Davies; Kasick; Chou; Nose; Hermann; Tucker; Official Journal of the American Academy of Otolaryngology vol. 1; No. 6; Dec. 1989.

Electronic Reanimation of Facial Paralysis—A Feasibility Study Rothstein et al. Otolaryngol Head Neck Surg 94:82 1986.

Tetanic Responses of Electrically Stimulated Paralyzed Muscle at Varying Interpulse Interval,S By Sara G. Carroll et al (IEEE Transactions on Biomedical Engineering vol. 36, No. 7 Jul. 1989).

Contralaterally Electrical Stimulation of Paralyzed Facial Muscles. Tobey DN, Sutton D. Otolaryngology (US) Sep.–Oct. 1978 86 (5) pORL 812–8 ISSN 0161–6439 Journal Code ON5.

*Primary Examiner*—Max Hindenburg
*Attorney, Agent, or Firm*—Harold R. Patton; Michael J. Jaro

[57] ABSTRACT

There is provided a system and method for detecting facial symmetry of patients with hemiparesis, or unilateral facial palsy, by facial impedance measurement which quantifies lack of facial symmetry and thereby provides a program for therapeutic stimulus of paralyzed facial muscles. A mid-line of facial current is generated between an upper electrode above the eyes and a lower electrode on the chin, the facial current being sub-threshold so as to avoid any muscle stimulus. Impedance measurements are taken by determining the voltage between symmetrically placed facial electrodes, or between electrode pairs consisting of one electrode positioned around the eye, cheek or mouth, and a reference electrode placed on the patient's chin so as to provide an effective bottom point of the Wheatstone bridge formed by the face. The voltage measurements translate into impedance measurements which are indicative of muscle paralysis, and provide a simple but reliable method of obtaining objective data useful for facial movement assessment. Objective current can be either sinusoidal or a train of pulses. In one specific embodiment, the measurement subsystem comprises a sigma-delta loop which includes the patient's face as a signal domain; the phase of the injected current is modulated in a manner similar to the negative feedback branch of a standard sigma-delta loop circuit, thereby providing a digital output which is relatively free of signal artifacts.

26 Claims, 4 Drawing Sheets

SYSTEM AND METHOD FOR DETECTING FACIAL SYMMETRY

FIELD OF THE INVENTION

This invention relates to systems and methods for measuring facial symmetry or facial movement of patients with unilateral facial palsy, so as to provide an objective quantitative analysis of facial conditions.

BACKGROUND OF THE INVENTION

Patients with hemiparesis, or unilateral facial palsy, can benefit from stimulus of the paralyzed muscles so as to restore facial symmetry. The treatment requires continual observation or evaluation, so that the stimulus can be adjusted to find optimum symmetry under most conditions. Such an evaluation requires recordation of clinically relevant facial movements, in a way that is objective and easy to operate. Such a method and system should be as patient-friendly as possible, and particularly not cause any patient pain. Thus, prior art techniques of actually stimulating facial muscles at different locations and measuring the responsive muscle contractions subjects the patient to painful episodes, and thus is not desirable. Any acceptable treatment should present only a minimum of mechanical load to the facial tissues. Further, since treatment options for unilateral facial palsy are diverse and each manifestation of the disability requires a specific approach, there is needed a reliable system and method which is flexible for evaluating different facial conditions, which can be used in daily clinical practice, and provides objective and reproducible data.

To date, many of the available facial measuring systems are subjective and are thus difficult to compare and standardize. In 1985, Brackman and House compiled a scoring system known as the "House-Brackman score." This system has the advantage of being simple easy-to-use in a clinical setting, and as gained widespread use. However, an examination of the scoring items used in this system indicate that the same score values can be obtained with substantially different disease expressions; further, it involves use of terms such as "slightly" and "severe" which are subjective, and thus make the data difficult to compare or standardize.

Other researchers have developed more objective scoring systems. For instance, Neely has described a computerized subtraction of video images of faces at rest and maximal excursion. More recently Frey has produced the "Faciometer," which comprises an electronic set of compasses which are held manually to the face, and which provide distance measurements in millimeters of displacement. These scoring systems are objective, relatively complete and reproducible, but are impractical and difficult to use in daily clinical practice. Measuring with these systems is time-consuming and a great amount of the data generated is difficult to interpret. Even more recently, in 1995, McGrouther introduced a combination of electromyography and surface laser scanning techniques, which provides objective, accurate and reproducible data, but again is very complicated and expensive, and has been used only in academic settings. A more simplified form of this technique, using only electromyography, has recently been reported, but in this more simplified form the technique is not practical for clinical use.

The current state of the art is thus such that there is a substantial need for a relatively inexpensive system which can find widespread acceptance in clinical settings, which is simple to use but flexible enough to accommodate different patient situations, and which provides reliable, objective, comparative data which is useful for assessing treatment for restoring facial symmetry.

SUMMARY OF THE INVENTION

The system of this invention provides for facial impedance measurement, and is based on the observation that movements between various anatomic landmarks on the surface of the skin correlate with changes in impedance between those landmarks. A transcutaneous electrical field is established by injecting a high frequency low strength current between two points in a vertical mid-facial line, such as from one electrode above the nose and one on the chin. The resulting electric field is symmetrical only to the degree that the patient has facial symmetry. Thus, a lack of facial symmetry means that there are unilateral facial impedance variations, such that the electric field at symmetrical facial points is not equal. The voltage differential between two symmetrical points on the face is thus a measure of impedance imbalance; as used hereafter, the terms of impedance and voltage are used synonymously. The injected signal may be analog, such as a 20 A rms 4 kHz sinusoidal current, or alternately may be in the form of series of low level pulses; in either form, the injected signal is a low level constant current signal which does not stimulate the nerves and does not induce patient discomfort.

At least a plurality of sensing electrodes are used for sensing the electrical field at different points on the face, to obtain impedance measurements which are indicative of the facial configuration. For example, a pair of sensing electrodes are placed symmetrically on the face, and the sensed voltage across them is representative of the lack of facial symmetry. Alternately, an impedance measurement can be taken between each of the symmetrical electrodes and a mid-line reference electrode on the chin, the impedance comparison providing a measure of facial symmetry. Additional electrodes can be positioned at different locations, such as near each eye and the respective corners of the mouth, to obtain measurements of impedance changes during a protocol of patient facial movements. The data from the measurements is suitably processed using a personal computer, a spreadsheet and a database program.

In another embodiment, which has the advantage of reducing artifacts in the sensed signal, a digital version of each detected impedance signal is obtained. In this arrangement, the injection signal and the impedance sense signal are incorporated with the face as part of a sigma-delta loop; the polarity of the injection current is reversed as a function of the output of the sigma-delta loop, with the sigma-delta converter delivering digital words representative of detected impedance, for further processing.

DESCRIPTION OF THE PREFERRED EMBODIMENTS

Figure 1:
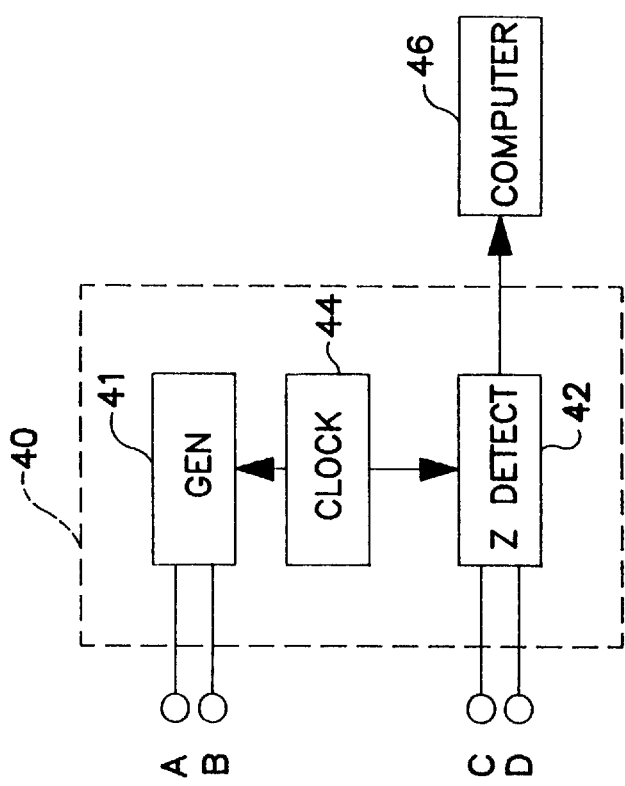
FIG. 1 is a schematic representation showing the main components of the system of this invention, including placement of electrodes on a patient's face.
Figure 1:
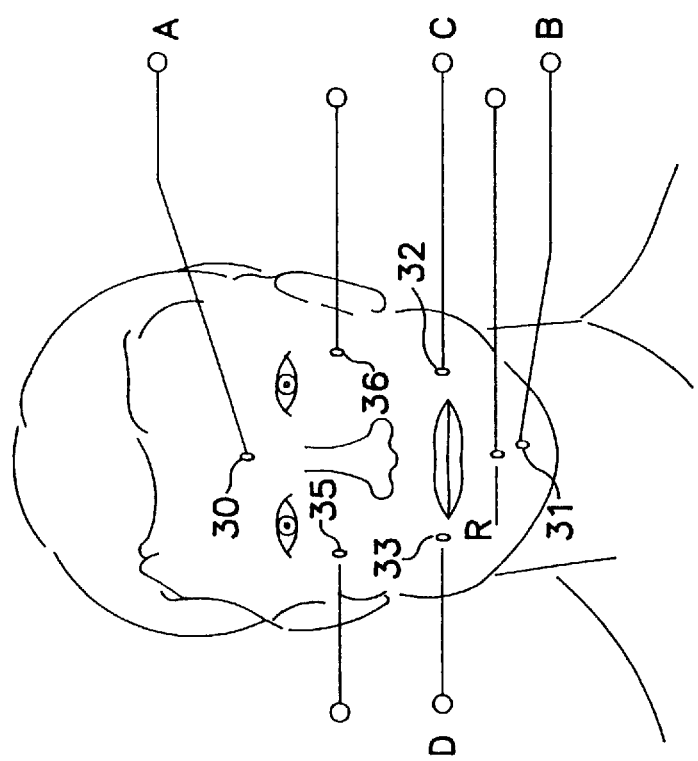

Referring now to FIG. 1, there is shown a depiction of a human face, with electrodes positioned thereon and a quadripolar impedance processing unit 40 which provides output signals and receives impedance measurement signals. Unit 40 may be any standard impedance meter, which provides a two-terminal output signal, and has a two-terminal voltage measuring circuit. As illustrated, a pair of electrodes 30, 31 are placed on a vertical mid-facial line, electrode 30 being illustrated above the nose and electrode being on the chin. These electrodes receive the output from generator 41, which is part of unit 40, which output is shown across output nodes A-B. This output is a relatively low amplitude sinusoidal signal, suitably at about 4 kHz and providing a current and of about 20 A rms. Assuming about 500 ohms across the injection electrodes, this results in about a 10 millivolt signal, well below what is required to stimulate tissue. Alternately, as discussed in connection with FIGS. 2A and 2B below, the signal may constitute square waves, or biphasic pulses, at, e.g., 128 Hz. Short duration pulses of about 30 microseconds, in the sub-milliamp range, likewise are below the stimulation threshold. Electrodes 30, 31 may be, for example, cutaneous encephalography electrodes, applied with standard EEG contact gel for obtaining optimal contact between electrodes and the skin. Whether sinusoidal or pulsed, the injected signal produces a transcutaneous electric field, oriented substantially along the facial mid-line.

A pair of electrodes 32, 33 is shown located symmetrically with respect to the mid-line defined by electrodes 30, 31. These electrodes are connected by conductors to input terminals C, D of unit 40, thereby being connected to an impedance meter as indicated as 42. Although not shown here, the electrode signals are suitably amplified, bandpass filtered, synchronous detected, and low pass filtered as part of the impedance measuring process. Of course, variations in the manner of measuring the impedance are within the scope of the invention. The meter is suitably designed to measure electrode impedances ranging from 100 ohms to 1k ohms.

In practice, by observing the voltage relationship between the injected current and the sensed field across electrodes 32, 33, the quadripolar unit 40 provides a very simple symmetry detector. The face provides the impedances of a Wheatstone bridge, and if there is facial symmetry, there is no voltage detected across electrodes 32, 33. Alternately, impedance measurements can be taken between one of the injection electrodes 30 or 31, and either electrode 32 or 33, and a reference electrode R positioned on the chin as a bottom of the facial Wheatstone bridge. Such a 4 pole measurement arrangement avoids the influence of the injection electrode-tissue interface. The measured impedance can be compared following different facial movements which are made by the patient to mimic certain conditions. Alternately, the impedances can be compared after each treatment, to detect impedance change as representing a change in facial symmetry. Likewise, impedance measurements can be made between either of electrodes 35 or 36 and reference electrode R. Thus, electrodes 35 and 36 may be placed proximate to the left and right eyes to detect muscle changes around the eyes following different proscribed movements made by the patient, e.g., assuming a poker face or closing the eyes firmly. Depending on the location of the sensing electrodes, the impedance measurements are related to specific facial locations.

Figure 2A:
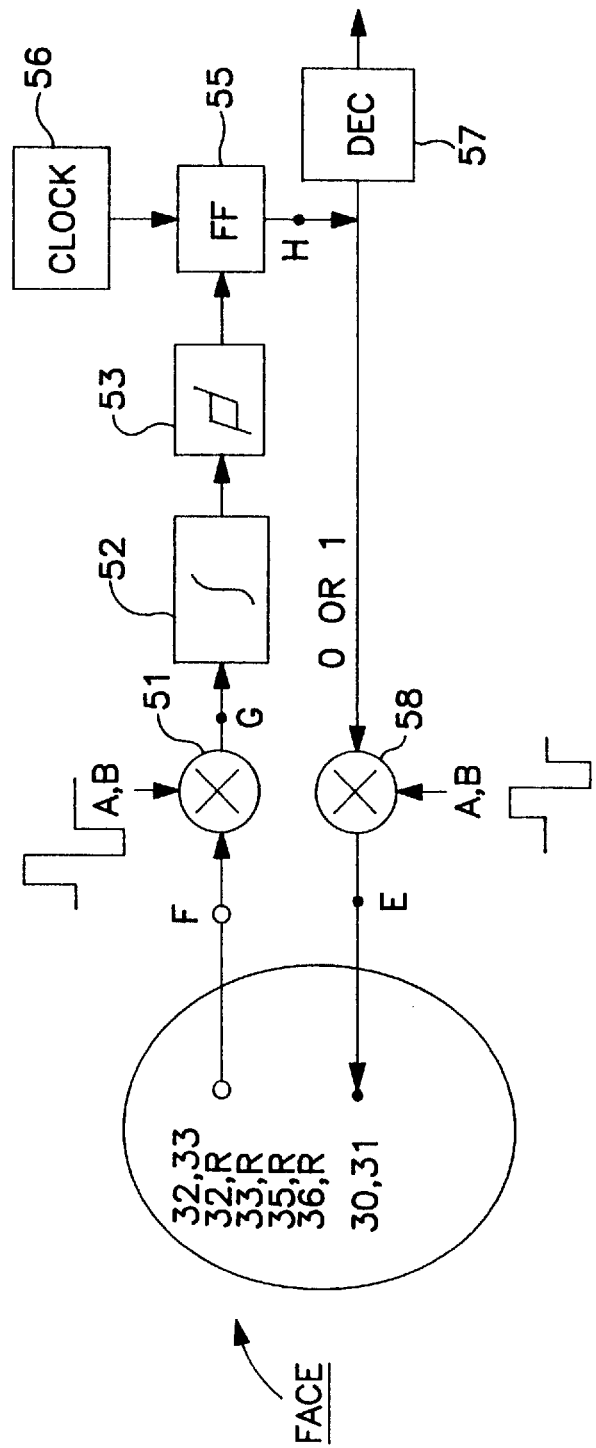
FIG. 2A is a block diagram of a digital version of an impedance-measuring circuit as used in the system of the this invention.
Figure 2B:
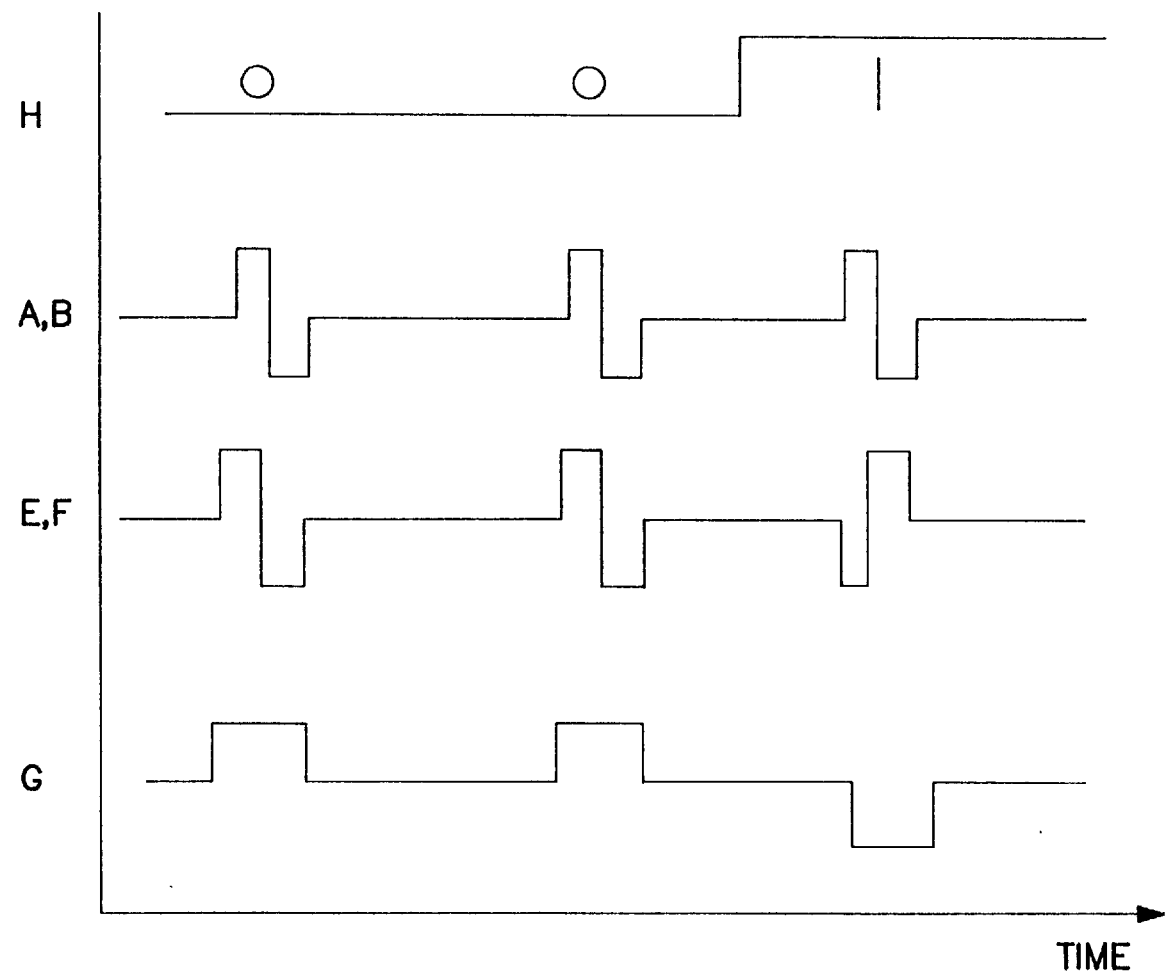
FIG. 2B is a set of timing diagrams illustrating operation of the circuit of FIG. 2A.

Still referring to FIG. 1, a clock 44 may be incorporated into unit 40, to synchronously control generation of injection pulses from generator 41, and detection of impedance by detector, or meter 42. Further, the detected impedance values are advantageously coupled to a computer 46, where a spreadsheet is used to record and process the data, particularly to derive relative numbers that are diagnostically meaningful. Referring now to FIG. 2A, there is shown a circuit block diagram of a digital configuration for measuring impedance. A reason for adopting this preferred embodiment is that the processing of the impedance signal in the presence of applied currents requires reduction of artifacts induced by the delivered or injected electrical currents, and the digital output is in a form for easy processing, e.g., baseline correction, filtering, and sample and hold. Further, as discussed below, this embodiment provides for digital correction of any asymmetry of the electrode placement.

The arrangement of FIG. 2A essentially provides for including the patient's face as part of a sigma-delta loop. The patient's face is indicated schematically at F, with the electrodes shown in FIG. 1 being illustrated. The inputted current is delivered from terminal E to mid-line electrodes 30, 31, and the impedance signal is obtained from electrode pair 32, 33 or any one of the sense electrode pairs discussed above, and connected to impedance sense terminal F. In the illustration of FIG. 2A, the injected signal is a series of biphasic pulses, as illustrated at the line designated A, B, in FIG. 2B. The injection signal is inputted to converter 58, where it is passed straight through if the other input is a logic zero; or is inverted if the logic input is a digital 1. The sensed signal, which is of the same form and polarity of the injected signal, is inputted to a like converter 51, which receives as its other input the biphasic signal from terminals A, B of unit 40, i.e., first a positive going and then a negative going pulse. The effect of converter 51 is to make the sensed impedance signal all positive or all negative, as seen at line G in FIG. 2B. The output from converter 51 is passed through integrator 52 and comparator 53. Comparator 53 is set with a reference point suitably about one-half of the maximum pulse input signal, and provides a positive output when the output from the integrator is above the reference point and a negative output when the integrator output is below the reference point. The output of the comparator is coupled to a flip-flop 55, which is clocked by a sigma-delta clock 56, such that the flip-flop output provides a one or zero following each sigma-delta clock. In practice, clock 56 may also be used to generate the injection signal, as illustrated at block 40 in FIG. 1.

The output of the sigma-delta loop, indicated at H, is coupled back to converter 58, to provide a form of negative feedback in the manner of a sigma-delta converter. Thus, when the output is high, or logic 1, the injection current is reversed at converter 58, as illustrated at the third biphasic pulse on the line indicated E, F of FIG. 2B. By this means, there is provided a closed-loop sigma-delta converter which provides a stream of logic signals. These logic signals are suitably inputted to a decimator 57, which accumulates a series of bit signals and outputs a digital word, e.g., a 32-bit word, at a suitable rate. By way of illustration, this system may use a series of 32 biphasic pulses, the respective series being delivered at about 128 Hz, which equates to a pulse rate of 4096 pulses per second; each biphasic pulse may be about 15 microseconds in duration. Alternately, the pulses may be spaced at any desired rate, with a sample and hold circuit being incorporated in the demodulator section to provide duty cycling.

In the arrangement of FIG. 2A, an adjustment can be made for any asymmetry in the placement of an electrode pair, e.g., pairs 32, 33 or 35, 36. This is done by inputting an appropriate correction factor to account for the observed asymmetrical placement, which is algebraically subtracted from the data output of decimator 57.

In practice, a continuous signal can be used in the sigma-delta circuit of FIG. 2A, instead of pulses. For example, the continuous wave can be modulated to yield a biphasic shift key (BPSK) signal, providing the negative feedback. In either case, the sigma-delta loop includes another signal domain, i.e., the human body.

Figure 3:
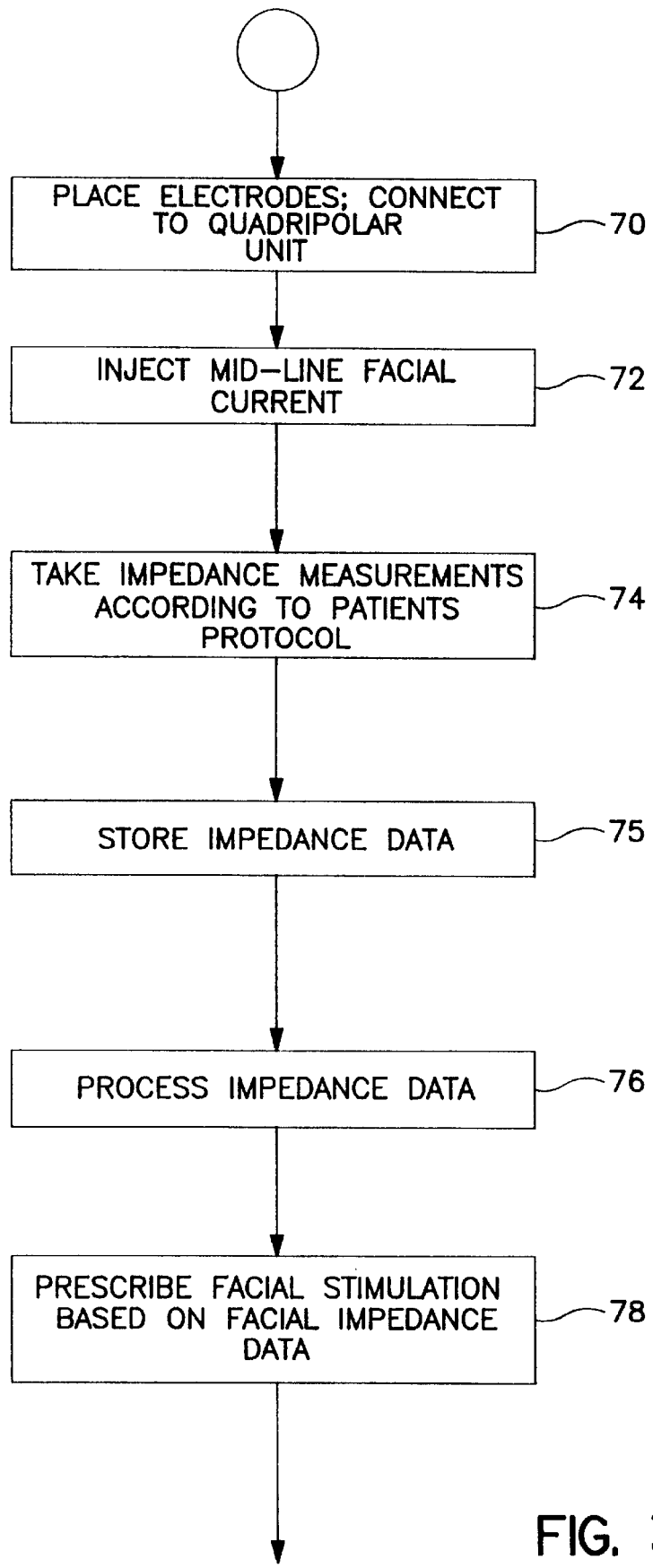
FIG. 3 is a flow chart showing the primary steps of a method of practicing this invention.

Referring now to FIG. 3, there is shown a simplified flow diagram illustrating the primary steps of practicing the method of this invention. As indicated at 70, electrodes are positioned on the patient, in accordance with the illustration of FIG. 1 and the discussion thereof. Next, the quadripolar unit is attached to the patient's face, the injection current output being coupled to the mid-line electrodes 30, 31, and a selected pair of sense electrodes being connected to terminals C, D for impedance detection. Following this, as illustrated at 72, the mid-line facial current is injected, this being either a sinusoidal or pulse current as discussed above. The next step, illustrated at 74, is to take impedance measurements according to a prescribed patient protocol. The measurement protocol directs the patient to make certain facial movements, or expressions; after each movement, an impedance measurement is taken between two electrodes separate from the electrodes supplying the injection signal. For example, left eye, right eye, left cheek, right cheek, left mouth and right mouth corner movements are instructed and performed by the patient, and the respective impedance changes are detected and recorded. At step 75, the impedance data is stored, and at step 76 it is processed, suitably with a PC and spreadsheet. While the invention does not embrace the specifics of the particular method of processing and expressing the data, it is preferred to process the data to produce relative numbers for comparison, and to thereby avoid expressions simply in absolute impedance readings which may vary from subject to subject, and thus have less diagnostic significance. After processing the impedance data, as illustrated at 78 the doctor may prescribe follow-up facial stimulation based on the facial impedance measurement that has been performed. More generally, the measuring system is used to follow the condition of patients and their response to therapy such as stimulation, surgery, mime exercise, etc. Alternately, a symmetry control stimulation system may be implanted, with a closed loop for adjusting stimulation as a function of impedance measurements.

The system and method of the preferred embodiments of this invention provide a substantial improvement over the prior art in terms of simplicity or ease of use; relatively low cost; and particularly in enabling collection of significant comparative data which can reliably be used to determine the state of facial paralysis and the need for stimulation. The impedance measurements obtained with the system of this invention provide objective indications of clinically relevant facial conditions and movements, and thus constitute an important improvement to meet a longstanding need in the field of facial movement assessment. The system and method can be carried out in either an analog or digital form; while preferred embodiments are illustrated, it is to be understood, that variations in terms of measuring instrumentation, and signal processing and data processing are within the scope of the invention.

I claim:

1. A facial impedance measurement system, for obtaining impedance measurements reflective of the condition of a patient's face, comprising:
    electric field means for generating an electric field oriented along a facial mid-line on said patient's face; and
    impedance means operative concurrently with said electric field means for determining an impedance value related to at least one location on said patient's face, said at least one location being displaced from said facial mid-line to obtain a measure of the patient's facial condition.

2. The system as described in claim 1, wherein said impedance means comprises 2 pole means for sensing voltage between said at least one location and a second location on the patient's face, said voltage being representative of said impedance value.

3. The system as described in claim 2, wherein said impedance means comprises means for sensing the voltage differential between said at least one location and a second location substantially symmetrical to said first location with respect to the facial mid-line.

4. The system as described in claim 2, wherein said impedance means comprises means for sensing the voltage differential between said at least one location and a second reference location positioned substantially on said facial mid-line.

5. The system as described in claim 1, wherein said electric field means comprises current injection means for injecting a transcutaneous electric field oriented substantially along said facial mid-line.

6. The system as described in claim 5, wherein said current injection means comprises a first electrode positioned above said patient's nose and a second electrode positioned on said patient's chin.

7. The system as described in claim 5, wherein said current injection means comprises analog means for generating an analog current.

8. The system as described in claim 7, wherein said analog means comprises sinusoidal means for generating a sinusoidal current of a value below what is required to stimulate the patient's facial tissue.

9. The system as described in claim 5, wherein said current injection means comprises digital means for injecting a pulsed current having an effective value less than that required to stimulate the patient's facial tissue.

10. The system as described in claim 1, wherein said sensing means comprises a sigma-delta loop circuit which interacts with the patient's face.

11. The system as described in claim 10, wherein said electric field means comprises pulse current injection means for injecting a pulsed current along said patient facial mid-line.

12. The system as described in claim 10, wherein said electric field means comprises current injection means for injecting a modulated sinusoidal current along said patient facial mid-line.

13. The system as described in claim 10, wherein said sigma-delta loop circuit comprises means for modulating said generated mid-line electric field as a function of said sensed voltage.

14. A facial impedance measurement system, comprising
    a first pair of electrodes positioned substantially mid-line on a patient's face;
    electric field means connected to said first pair of electrodes for generating an electric field pattern on said patient's face;
    a second pair of electrodes positioned on said patient's face, at least one of said electrodes being positioned at a prescribed facial location off of the patient's facial mid-line; and
    impedance detection means connected to said second pair of electrodes for obtaining a voltage measurement across said second pair of electrodes which is indicative of patient facial impedance relating to said prescribed location.

15. The system as described in claim 14, comprising a quadripolar impedance processing unit.

16. The system as described in claim 14, wherein said second pair of electrodes comprises electrodes placed symmetrically on said patient's face with respect to the patient's facial mid-line.

17. The system as described in claim 14, wherein said second pair of electrodes comprises a reference electrode placed substantially on said patient facial mid-line.

18. The system as described in claim 14, wherein said impedance sensing means comprises means for detecting a sinusoidal voltage.

19. The system as described in claim 14, wherein said sensing means comprises means for detecting a pulsed signal.

20. A method of facial impedance measurement, comprising:

positioning a pair of injection electrodes substantially mid-line on the patient's face, and connecting an electrical generator thereto to generate a transcutaneous electric field between said pair of injection electrodes;

positioning a pair of sensing electrodes on the patient's face, at least one of said sensing electrodes being positioned laterally away from said mid-line; and obtaining impedance data from said sensing electrodes, said impedance data being reflective of the patient's facial symmetry.

21. The method as described in claim 20, comprising positioning a plurality of sensing electrodes at respective off mid-line locations on said patient's face, positioning one of said sensing electrodes as a reference electrode substantially on said mid-line, and obtaining an impedance measurement between to each of said sensing electrodes and said reference electrode.

22. The method as described in claim 21, comprising processing said impedance data to provide comparative measurements reflective of facial impedance at said respective locations.

23. The method as described in claim 21, comprising injecting a pulsed signal along said injection electrodes, and deriving four said sensing electrodes digital word representations of patient facial impedance.

24. The method as described in claim 23, comprising connecting sigma-delta circuitry to one of said plurality of sensing electrodes and said reference electrodes, and using said patient's face with said circuitry to form a sigma-delta loop.

25. The method as described in claim 20, comprising injecting a sinusoidal current of an amount below threshold for stimulating said patient's face.

26. A method of facial impedance measurement, comprising:

establishing and carrying out a protocol of patient facial movements, each movement relating to a facial position;

injecting a transcutaneous current substantially mid-line along a patient's face, thereby establishing an electric field relative to said mid-line; and following each of said facial movements, obtaining a measure of the facial impedance between the related facial position and a reference position.

\* \* \* \* \*